United States Patent
Feldman et al.

[11] Patent Number: 6,075,608
[45] Date of Patent: Jun. 13, 2000

[54] BLEND SEGREGATION DETECTION

[75] Inventors: Sandra Freedman Feldman, Niskayuna; Angel Luis Ortiz, Jr., Ballston Spa, both of N.Y.; Robert William Foster, Evansville, Ind.

[73] Assignee: General Electric Company, Schenectady, N.Y.

[21] Appl. No.: 09/075,913

[22] Filed: May 11, 1998

[51] Int. Cl.[7] .................................................. G01B 11/00
[52] U.S. Cl. .......................... 356/406; 356/407; 356/425
[58] Field of Search ...................................... 356/406, 407, 356/425, 409, 410, 445

[56] References Cited

U.S. PATENT DOCUMENTS

| | | | |
|---|---|---|---|
| 5,284,137 | 2/1994 | Kessler et al. | 128/633 |
| 5,559,173 | 9/1996 | Campo et al. | 523/303 |
| 5,590,251 | 12/1996 | Takagi | 395/131 |
| 5,642,192 | 6/1997 | Gordon et al. | 356/328 |
| 5,650,942 | 7/1997 | Granger | 364/526 |
| 5,859,708 | 1/1999 | Feldman | 356/406 |

OTHER PUBLICATIONS

M.D. Ashton et al., "The Use of a Light Probe for Assessing the Homogeneity of Powder Mixtures," Chemical Engineering Science, 1966, vol. 21, pp. 843–849.

R. Weinekotter et al., "Characterization of Particulate Mixtures by In-Line Measurements," Part. Part. Syst. Charact. 11 (1994) pp. 284–290.

*Primary Examiner*—Frank G. Font
*Assistant Examiner*—Reginald A. Ratliff
*Attorney, Agent, or Firm*—Patrick K. Patnode; Marvin Snyder

[57] ABSTRACT

An apparatus for sensing blend segregation in a mixture comprises a light transmissive window disposed within a feed connection between a hopper and an extruder for example, a light source for emitting a light beam, and a light sensor to perform spectrum analysis of any incident light supplied thereto. An illumination assembly has a first end optically coupled to the light source and a second end optically coupled to the light transmissive window to illuminate a portion of the internal path provided by the feed connection. At least one detection assembly is provided, having a first end disposed adjacent to the light transmissive window so as to detect the reflection from any illuminated polymer blend passing therethrough. The light sensor collects the diffuse reflecting light from the polymer blend and transforms the diffuse reflecting light into tri-color signals, reflection curves or the like, for comparison with other diffuse reflecting light so as to determine if a particular blend is segregating.

24 Claims, 2 Drawing Sheets

BLEND SEGREGATION DETECTION

CROSS-REFERENCE TO RELATED APPLICATION

This invention is related to commonly assigned patent application Ser. No. 08/926,084, filed Sep. 2, 1997, entitled "Sensing Blend Color Homogeneity" which application is herein incorporated by reference.

BACKGROUND OF THE INVENTION

This application relates generally to plastics processing, and in particular relates to sensing blend component segregation during plastics processing.

Modern plastic materials have found a wide range of markets and a variety of applications in diverse manufacturing fields. These plastic materials offer many desirable characteristics such as an excellent finish, desirable electrical, thermal and mechanical properties, low cost and a variety of colors.

Plastics are typically formed of one or more base polymers or resins, one or more colorants, and other additives. Such additives may include, for example, fiberglass for structural reinforcement, flame retardants, plasticizers, or mold release agents. The plastics are manufactured by initially mixing these components to form a substantially homogeneous polymer blend. The polymer blend then typically undergoes extrusion, or the like, to form a raw product, for example pellets. The raw products are then utilized to produce final polymer products of various forms.

During a typical finishing process, the base polymers or resins, the colorants, and other additives are fed from one or more hoppers into an extruder or the like.

During continuous feed processes, the polymer blend will fill a column connecting the hopper and the extruder. If the constituent parts of the polymer blend comprise particles of differing sizes and weights, segregation may occur in the column. The segregation of the particles, over the course of a manufacturing cycle, may be severe.

Vibrations in the system tend to cause powder constituents to migrate toward the bottom of the column, while larger constituents and pellets tend to migrate toward the top of the column. This variability within the material blend fed to the extruder will create undesirable variability in the final products.

Accordingly, it is desired to improve the process of constituent intermixing in the production of a polymer product from base resins and colorants.

SUMMARY OF THE INVENTION

An apparatus for sensing blend segregation in a mixture comprises a light transmissive window disposed within a feed connection between a hopper and an extruder, for example, a light source for emitting a light beam, and a light sensor to perform spectrum analysis of any incident light supplied thereto. An illumination assembly has a first end optically coupled to the light source and a second end optically coupled to the light transmissive window to illuminate a portion of the internal path provided by the feed connection. At least one detection assembly is provided, having a first end disposed adjacent to the light transmissive window so as to detect the reflection from any illuminated polymer blend passing therethrough. The light sensor collects the diffuse reflecting light from the polymer blend and transforms the diffuse reflecting light into tri-color signals, reflection curves or the like, for comparison with a desired reflectance or for evaluating changes in the diffuse reflection over time so as to determine if a particular blend is segregating.

DETAILED DESCRIPTION OF THE INVENTION

Figure 1:
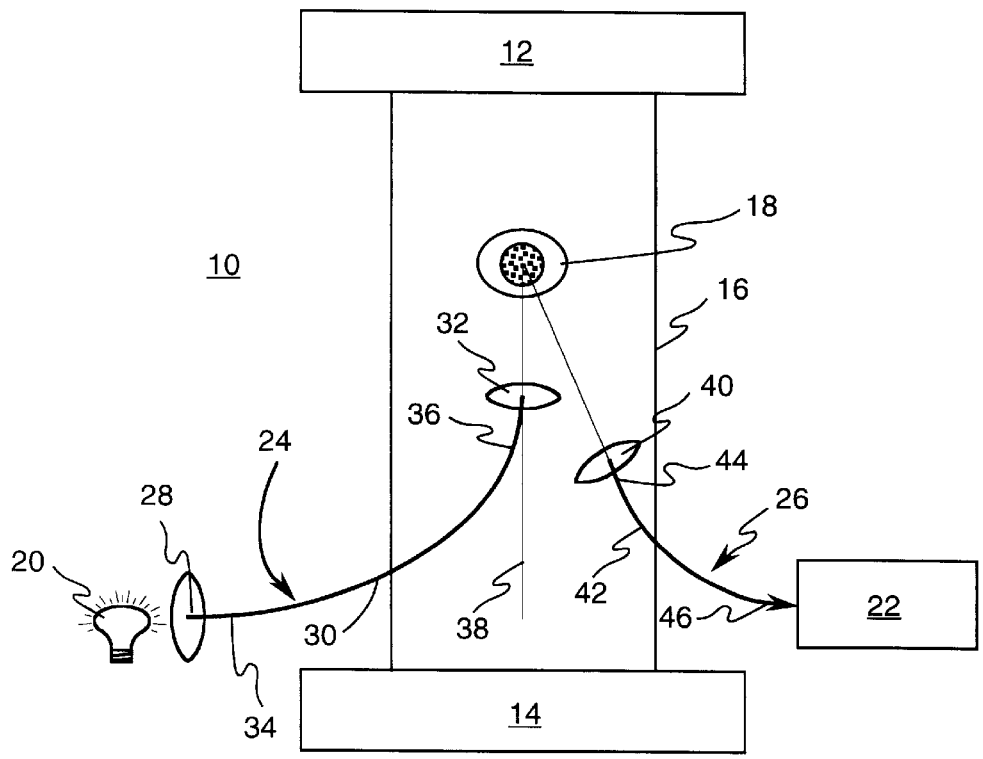
FIG. 1 is a schematic illustration of one embodiment of the instant invention.

An apparatus for sensing blend segregation 10 comprises at least one hopper 12 or the like coupled to an extruder 14 or the like, as shown in FIG. 1. A feed connection 16 is disposed between hopper 12 and extruder 14 to provide a path for a continuous feed of a polymer blend from hopper 12 to extruder 14.

Apparatus for sensing blend segregation 10 further comprises a light transmissive window 18 disposed within a sidewall of feed connection 16, a light source 20, a light sensor 22, an illumination assembly 24, and a detection assembly 26.

Light transmissive window 18 should be optically transparent. In one embodiment, light transmissive window 18 comprises a quartz material or the like.

Light source 20 is provided for emitting and projecting a light beam to light transmissive window 18. Light source 20 may include any light source capable of providing a spectrum through the visible light region, typically avoiding fluorescence. In one embodiment, light source 20 emits a light beam at a wavelength in the range between about 400 nm to about 770 nm. In one embodiment, light source 20 comprises a tungsten-halogen light source.

Light sensor 22 may comprise a spectrometer, a spectrophotometer, a spectrocolorimeter, a spectrophotometric colorimeter, or the like, to perform spectrum analysis of any incident light supplied thereto.

Illumination assembly 24 comprises a first lens 28, an optical fiber 30, and a second lens 32. First lens 28 is disposed to receive light emitted from light source 20. First lens 28 typically comprises a planoconvex lens or the like. A light source end 34 of optical fiber 30 is aligned with first lens 28 and an injection end 36 of optical fiber 30 is at second lens 32 to provide an optical coupling therebetween. The light beam is emitted from light source 20 and is injected into light source end 34 of optical fiber 30.

Injection end 36 of optical fiber 30 is typically, although not necessarily, disposed normal to and proximate light transmissive window 18. Second lens 32 is positioned adjacent light transmissive window 18. The light beam injected into optical fiber 30 passes through injection end 36 of optical fiber 30 and is projected onto light transmissive window 18 so as to illuminate a portion of the internal path provided by feed connection 16 and typically a portion of polymer blend passing therethrough.

Detection assembly 26 comprises a first detection lens 40 and an optical fiber 42. First detection lens 40 is typically, although not necessarily, disposed adjacent to light transmissive window 18 at an angle ($\alpha$) with respect to a reference axis 38 so as to detect diffuse reflection from the illuminated portion within feed connection 16. Reference axis 38 is aligned essentially perpendicular to light transmissive window 18.

In one embodiment of the instant invention, angle (α) is in the range between about 1° to about 89°. In another embodiment of the instant invention, angle (α) is in the range between about 30° to about 60°.

A first end 44 of optical fiber 42 is optically coupled to first detection lens 40 such that diffuse reflection directed into first detection lens 40 is injected into first end 44 of optical fiber 42. The diffuse reflection is transmitted through optical fiber 42 to a second end 46 of optical fiber 42, which second end 46 is optically coupled to light sensor 22.

Although the present invention is described as including a single detection assembly 26, the present invention is not limited to practice with a single detection assembly 26. In fact, the present invention can be implemented and utilized with many other configurations. For example, two or more detection assemblies may be utilized within the present invention.

Light sensor 22 senses the light transmitted through optical fiber 42. The collected light from optical fiber 42 is transformed by light sensor 22 into signals providing spectral information, for example L, a, b values, RGB, xyz or the like, or into reflectances at selected wavelengths or various reflectance curves.

In one embodiment of the instant invention, light sensor 22 provides spectral information about the collected light by measuring the diffusely reflected spectrum from a polymer blend passing through feed connection 16 and transforms the measured spectrum into standard tri-color signals like L, a, b signals or the like.

For purposes of discussion, tri-color signals will be discussed in terms of L, a, b coordinate system wherein the lightness is typically called L, the red-green coordinate is called a, (positive for red colors and negative for green colors) and the yellow-blue coordinate is called b, (positive for yellow colors and negative for blue colors). This L, a, b coordinate system is a color measuring system that is currently utilized and known in the art. The utilization of the L, a, b coordinate system within this application is for purposes of discussion only and is not a limitation of the instant invention. In fact, the instant invention can be utilized with any known color measurement system.

This process of transforming the collected light into tri-colored signals is performed at a number of timed intervals during a polymer blend run, typically in the range between about 1 sample per second to about 1 sample per minute.

In one embodiment of the instant invention, the tri-color signals generated by light sensor 22 are maintained as a function of time to check for statistically significant changes. For example, if the tri-color signals are generated and monitored one time each five seconds you receive twelve readings each minute. Over a predetermined window of time (one minute for example) a system user may receive a range of values having a low standard deviation. While monitoring the system, in a second predetermined window of time, a system user may receive a range of values having a greater standard deviation, an indication that the mix is less homogeneous due to segregation.

Another option is to use standard SPC (statistical process control) routines on the L,a,b measurements: Typical rules may include watching for any points outside of the control limits, nine consecutive points on one side of the average, or six consecutively increasing or decreasing points. Exact rules would need to be formulated after observing typical data generated under operating conditions. These could be done on individual measurements or on averages of several consecutive measurements.

Another option is to calculate the color difference ΔE between measurements taken at the beginning of the cycle and measurements taken at intervals thereafter. (Measurements all are calculated from the original color.) Several color differences of greater than 1 unit suggest that the overall color of the blend is shifting, indicating segregation from the beginning to the end of the cycle. Again, the calculation could be done on individual measurements or the average of several consecutive measurements.

In another embodiment of the instant invention, a comparison of the current spectral distribution is made with respect to a previous spectral distribution. For example, if in a previous spectral distribution there were ten tri-color signals clustered around color "x" and two tri-color readings clustered around color "y" and in a current spectral distribution the tri-color signals are equally clustered around color "x" and color "y" (six apiece), a system user would be able to determine a change in spectral distribution due to segregation.

In another embodiment of the instant invention, light sensor 22 provides spectral information about the collected light by measuring the diffusely reflected spectrum from a polymer blend passing through feed connection 16. The reflectance at selected wavelengths would be utilized in a direct-read embodiment.

If, for example, a blend passing through feed connection 16 having a variety of pigments, additives and pellets consists of a known color, a system user can study a selected wavelength region. If, for example, the blend were nominally red, a system user can look at the spectral reflectance at about 630 nm, where a red blend would be expected to peak. When a red mix passes through feed connection 16 a signal approaching 630 nm is received. When another constituent blend part passes through feed connection 16 a different signal is received. If a system user analyzes the distribution and occurrence of signals and the variance over time, an indication of blend segregation would become apparent.

In another embodiment of the instant invention, diffuse reflectance curves for a large number of constituent parts of various polymer blends are measured and stored in advance in a library, a lookup table or the like. Light sensor 22 provides a system user with spectral reflectance curves. A stored reflectance curve may then be reconstructed as the combination of its constituents and the concentration of each constituent determined. Once the constituent parts and concentrations are determined, these constituent parts can be compared with the known mixture to determine if segregation is occurring. This set up may be further refined to compare the blend over time to see if segregation occurs over time.

Figure 2:
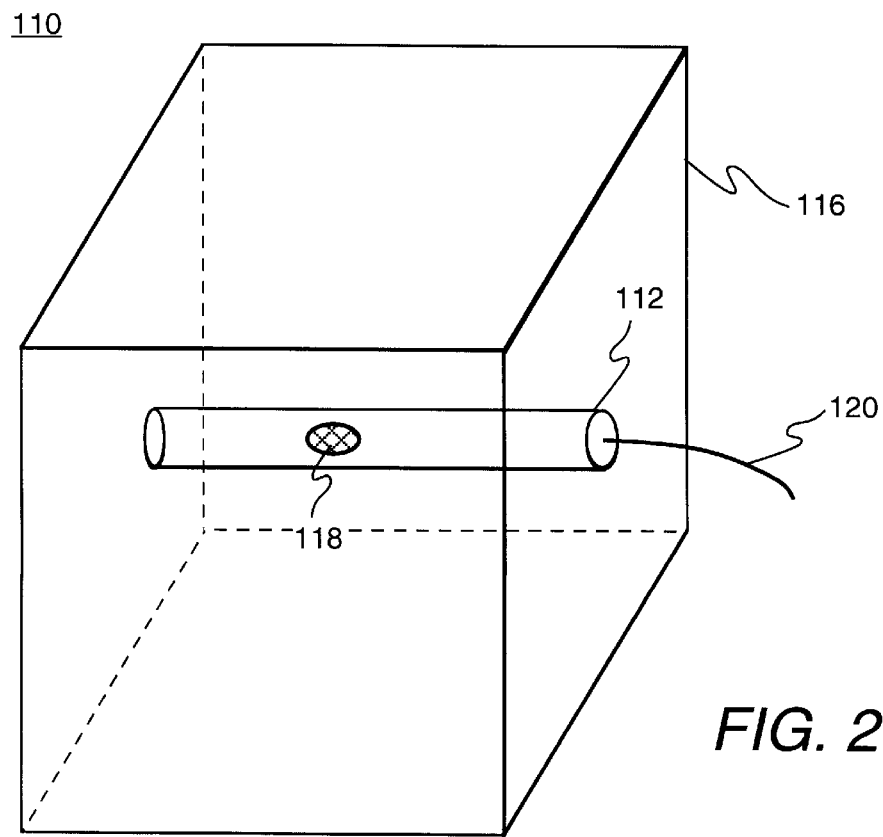
FIG. 2 is a schematic illustration of another embodiment of the instant invention.

In accordance with another embodiment of the instant invention, an in-line apparatus for sensing blend segregation 110 comprises an internal detection tube 112 disposed within a feed connection 116, as shown in FIG. 2. Feed connection 116 is typically disposed between a hopper (not shown) and an extruder (not shown) or the like so as to provide a path for a continuous feed of polymer blend.

Internal detection tube 112 further comprises a light transmissive window 118 disposed within a sidewall of internal detection tube 112 and a fiber optics bundle 120 disposed within internal detection tube 112. Internal detection tube 112 is typically a cylindrical tube or a diamond shaped conduit so as to offer the least interference to material blend passing thereabout.

Light transmissive window 118 should be optically transparent. In one embodiment, light transmissive window 118 comprises a quartz material or the like. Light transmissive window 118 is typically disposed on an upper portion of internal detection tube 112 such that an optimal view of material passing over internal detection tube 112 is received.

Internal detection tube 112 is disposed within feed connection 116 in a manner so as to minimize the disturbance of the flow of polymer blend therethrough.

Figure 3:
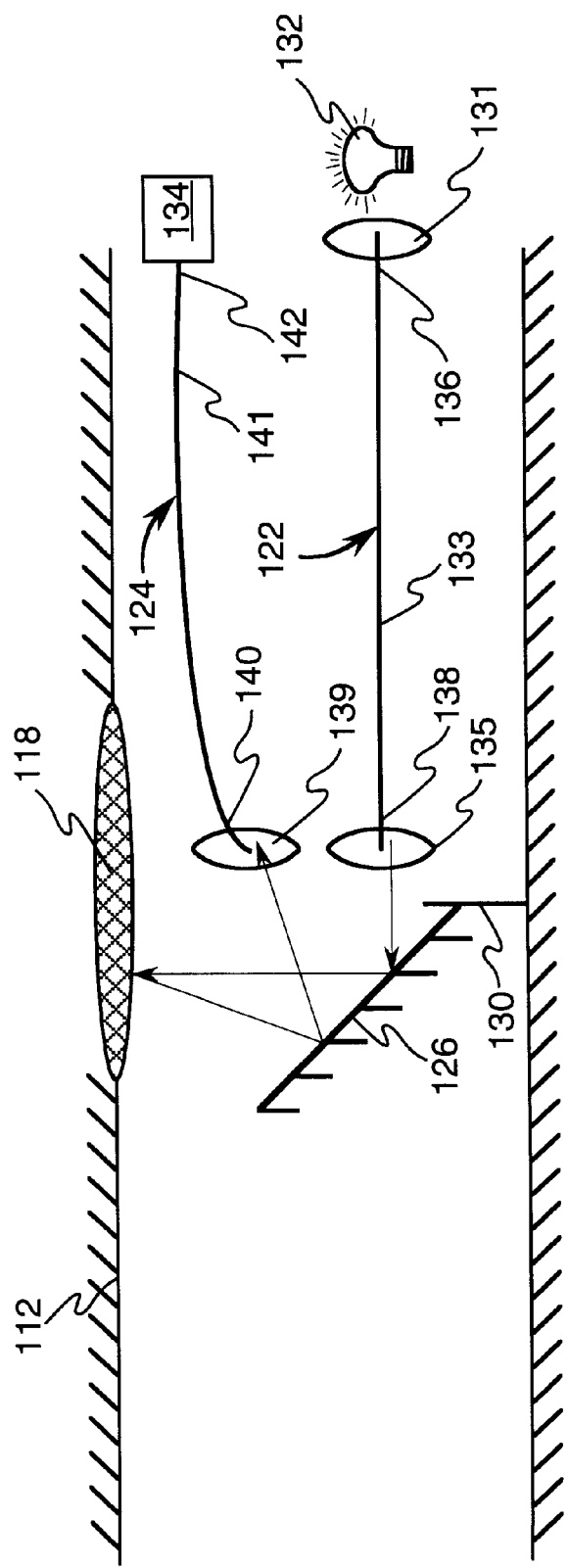
FIG. 3 is an exploded schematic view of one embodiment of the illumination and detection assemblies of FIG. 2.

Fiber optics bundle 120 comprises an illumination assembly 122 and a detection assembly 124, as shown in FIG. 3. Typically, fiber optics bundle 120 further comprises a mirror 126 disposed within internal detection tube 112 adjacent light transmissive window 118. In one embodiment, mirror 126 is disposed at a nominal angle ($\alpha$) of 45°, with respect to a reference line 130. Reference line 130 is disposed essentially perpendicular to light transmissive window 118. In one embodiment of the instant invention, angle ($\alpha$) is in the range between about 1° to about 89°. In another embodiment of the instant invention, angle ($\alpha$) is in the range between about 30° to about 60°.

A light source 132 is provided for emitting and projecting a light beam to light transmissive window 118. Light source 132 may include any light source capable of providing a spectrum through the visible light region, typically avoiding fluorescence. In one embodiment, light source 132 emits a light beam at a wavelength in the range between about 400 nm to about 700 nm. In one embodiment light source 132 comprises a tungsten-halogen light source.

A light sensor 134 is provided to perform spectrum analysis of any incident light supplied thereto. Light sensor 134 may comprise a spectrometer, a spectrophotometer, a spectrocolorimeter, a spectrophotometric calorimeter, or the like.

Illumination assembly 122 comprises a first lens 131, an optical fiber 133, and a second lens 135. First lens 131 is disposed to receive light emitted from light source 132. First lens 131 typically comprises a planoconvex lens or the like. A light source end 136 of optical fiber 133 is aligned with first lens 131 and an injection end 138 of optical fiber 133 is at second lens 135 to provide an optical coupling therebetween. The light beam is emitted from light source 132 and is injected into light source end 136 of optical fiber 133

Injection end 138 of optical fiber 133 is disposed proximate to light transmissive window 118. Second lens 135 is positioned adjacent light transmissive window 118. The light beam injected into optical fiber 133 passes through injection end 138 of optical fiber 133 and is projected onto mirror 126. Mirror 126 directs the light beam onto light transmissive window 118 so as to illuminate a portion of the internal path provided by feed connection 116 and typically a portion of polymer blend passing therethrough.

Detection assembly 124 comprises a first detection lens 139 and an optical fiber 141. First detection lens 139 is typically, although not necessarily, disposed adjacent to light transmissive plate 118 at an angle ($\alpha$) with respect to mirror 126 so as to detect diffuse reflection from the illuminated portion within feed connection 116 (FIG. 2).

A first end 140 of optical fiber 141 is optically coupled to first detection lens 139 such that diffuse reflection directed into first detection lens 139 is injected into first end 140 of optical fiber 141. The diffuse reflection is transmitted through optical fiber 141 to a second end 142 of optical fiber 141, which second end 142 is optically coupled to light sensor 134.

Light sensor 134 senses the light transmitted through optical fiber 141. The collected light from optical fiber 141 is transformed by light sensor 134 into signals providing spectral information, for example L, a, b values, RGB, xyz or the like, or into reflectances at selected wavelengths or various reflectance curves.

In one embodiment of the instant invention, light sensor 134 provides spectral information about the collected light by measuring the diffusely reflected spectrum from a polymer blend passing through feed connection 116 (FIG. 2) and transforms the measured spectrum into standard tri-color signals like L, a, b signals or the like.

This process of transforming the collected light into tri-colored signals is performed at a number of timed intervals during a polymer blend run, typically in the range between about1 sample per second to about1 sample per minute.

In one embodiment of the instant invention, the tri-color signals generated by light sensor 134 are maintained as a function of time to check for statistically significant changes. For example, if the tri-color signals are generated and monitored one time each five seconds you receive twelve readings each minute. Over a predetermined window of time (one minute for example) a system user may receive a range of values having a low standard deviation. While monitoring the system, in a second predetermined window of time, a system user may receive a range of values having a greater standard deviation, an indication that the mix is less homogeneous due to segregation.

Another option is to use standard SPC (statistical process control) routines on the L,a,b measurements: Typical rules may include watching for any points outside of the control limits, nine consecutive points on one side of the average, or six consecutively increasing or decreasing points. Exact rules would need to be formulated after observing typical data generated under operating conditions. These could be done on individual measurements or on averages of several consecutive measurements.

Another option is to calculate the color difference $\Delta E$ between measurements taken at the beginning of the cycle and measurements taken at intervals thereafter. (Measurements all are calculated from the original color.) Several color differences of greater than 1 unit suggest that the overall color of the blend is shifting, indicating segregation from the beginning to the end of the cycle. Again, the calculation could be done on individual measurements or on the average of several consecutive measurements.

In another embodiment of the instant invention, a comparison of the current spectral distribution is made with respect to a previous spectral distribution. For example, if in a previous spectral distribution there were ten tri-color signals clustered around color "x" and two tri-color readings clustered around color "y" and in a current spectral distribution the tri-color signals are equally clustered around color "x" and color "y" (six apiece), a system user would be able to determine a change in spectral distribution due to segregation.

In another embodiment of the instant invention, light sensor 134 provides spectral information about the collected light by measuring the diffusely reflected spectrum from a polymer blend passing through feed connection 116 (FIG. 2). The reflectance at selected wavelengths would be utilized in a direct-read embodiment.

If, for example, a blend passing through feed connection 116 (FIG. 2) having a variety of pigments, additives and pellets consists of a known color, a system user can study a selected wavelength region. If, for example, the blend were nominally red, a system user can look at the spectral reflectance at about 630 nm, where a red blend would be expected to peak. When a red mix passes through feed connection 116 (FIG. 2) a signal approaching 630 nm is received. When another constituent blend part passes through feed connection 116 (FIG. 2) a different signal is received. If a system user analyzes the distribution and occurrence of signals and the variance over time, an indication of blend segregation would become apparent.

In another embodiment of the instant invention, diffuse reflectance curves for a large number of constituent parts of various polymer blends are measured and stored in advance in a library, a lookup table or the like. Light sensor 134 provides a system user with spectral reflectance curves. A stored reflectance may then be reconstructed as the combination of its constituents and the concentration of each constituent determined. Once the constituent parts are determined, these constituent parts can be compared with the known mixture to determine if segregation is occurring. This set up may be further refined to compare the blend over time to see if segregation occurs over time.

While only certain features of the invention have been illustrated and described, many modifications and changes will occur to those skilled in the art. It is, therefore, to be understood that the appended claims are intended to cover all such modifications and changes as fall within the true spirit of the invention.

What is claimed is:

1. An apparatus for sensing blend segregation comprising:
   at least one hopper;
   an extruder;
   a feed connection disposed between said at least one hopper and said extruder so as to provide a path for a continuous feed of a polymer blend from said at least one hopper to said extruder;
   a light transmissive window disposed within a sidewall of said feed connection;
   an illumination assembly;
   a detection assembly;
   a light source for emitting a light beam; and
   a light sensor;
   wherein said illumination assembly has a first end optically coupled to said light source and a second end optically coupled to said light transmissive window so as to illuminate a portion of an internal path defined by said feed connection and said polymer blend therein;
   wherein said detection assembly has a first end disposed adjacent said light transmissive window so as to detect any diffuse reflection from the illumination of said polymer blend and a second end optically coupled to said light sensor;
   wherein said light sensor collects said diffuse reflecting light from said detection assembly and transforms said diffuse reflecting light into signals so as to determine if said polymer blend is segregating.

2. An apparatus for sensing blend segregation, in accordance with claim 1, wherein said light transmissive plate is optically transparent.

3. An apparatus for sensing blend segregation in accordance with claim 1, wherein said light transmissive plate comprises a quartz material.

4. An apparatus in accordance with claim 1, wherein said light source comprises any light source capable of providing a spectrum through the visible light region.

5. An apparatus in accordance with claim 1, wherein said light source emits a light beam at a wavelength in the range between about 400 nm to about 770 nm.

6. An apparatus in accordance with claim 1, wherein said light source comprises a tungsten-halogen light source.

7. An apparatus in accordance with claim 1, wherein said color sensor is selected from the group consisting of a spectrometer, a spectrophotometer, a spectrocolorimeter, and a spectrophotometric calorimeter.

8. An apparatus in accordance with claim 1, wherein said illumination assembly comprises a first lens disposed adjacent said light source, an optical fiber having a light source end aligned with said first lens so as to complete an optical coupling at said light source and a second lens disposed adjacent said light transmissive window so as to intercept said light beam injected into said optical fiber and project said light beam onto said light transmissive plate so as to illuminate said polymer blend.

9. An apparatus in accordance with claim 1, wherein said detection assembly comprises a first lens disposed adjacent said light transmissive window at an angle ($\alpha$) with respect to a reference axis so as to detect diffuse reflection from said illuminated polymer blend and an optical fiber coupled to said light sensor so as to transmit said diffuse reflection from said first detection lens to said light sensor.

10. An apparatus in accordance with claim 1, wherein the signals generated by said light sensor are maintained as a function of time to check for statistically significant changes.

11. An apparatus in accordance with claim 1, wherein a first spectral distribution is compared with a second spectral distribution to determine a change in spectral distribution due to segregation.

12. An apparatus in accordance with claim 1, wherein the diffuse reflectance curves for a number of polymer blend constituent parts are stored in advance in a library or lookup table for comparison with a measured reflectance curve.

13. An apparatus for sensing blend segregation comprising:
   at least one hopper;
   an extruder;
   a feed connection disposed between said at least one hopper and said extruder so as to provide a path for a continuous feed of a polymer blend from said at least one hopper to said extruder;
   in internal detection tube disposed within said feed connection;
   a light transmissive window disposed within a sidewall of said internal detection tube;
   an illumination assembly and a detection assembly disposed within said detection tube;
   a light source for emitting a light beam; and
   a light sensor;
   wherein said illumination assembly has a first end optically coupled to said light source and a second end optically coupled to said light transmissive window so as to illuminate a portion of an internal path defined by said feed connection and said polymer blend therein;
   wherein said detection assembly has a first end disposed adjacent said light transmissive window so as to detect any diffuse reflection from the illumination of said polymer blend and a second end optically coupled to said light sensor;
   wherein said light sensor collects said diffuse reflecting light from said detection assembly and transforms said diffuse reflecting light into signals so as to determine if said polymer blend is segregating.

14. An apparatus for sensing blend segregation, in accordance with claim 13, wherein said light transmissive plate is optically transparent.

15. An apparatus for sensing blend segregation in accordance with claim 13, wherein said light transmissive plate comprises a quartz material.

16. An apparatus in accordance with claim 13, wherein said light source comprises any light source capable of providing a spectrum through the visible light region.

17. An apparatus in accordance with claim 13, wherein said light source emits a light beam at a wavelength in the range between about 400 nm to about 770 nm.

18. An apparatus in accordance with claim 13, wherein said light source comprises a tungsten-halogen light source.

19. An apparatus in accordance with claim 13, wherein said color sensor is selected from the group consisting of a spectrometer, a spectrophotometer, a spectrocolorimeter, and a spectrophotometric colorimeter.

20. An apparatus in accordance with claim 13, wherein said illumination assembly comprises a first lens disposed adjacent said light source, an optical fiber having a light source end aligned with said first lens so as to complete an optical coupling at said light source and a second lens disposed adjacent said light transmissive window so as to intercept said light beam injected into said optical fiber and project said light beam onto said light transmissive plate so as to illuminate said polymer blend.

21. An apparatus in accordance with claim 13, wherein said detection assembly comprises a first lens disposed adjacent said light transmissive window at an angle ($\alpha$) with respect to a reference axis so as to detect diffuse reflection from said illuminated polymer blend and an optical fiber coupled to said light sensor so as to transmit said diffuse reflection from said first detection lens to said light sensor.

22. An apparatus in accordance with claim 13, wherein the signals generated by said light sensor are maintained as a function of time to check for statistically significant changes.

23. An apparatus in accordance with claim 13, wherein a first spectral distribution is compared with a second spectral distribution to determine a change in spectral distribution due to segregation.

24. An apparatus in accordance with claim 13, wherein the diffuse reflectance curves for a number of polymer blend constituent parts are stored in advance in a library or lookup table for comparison with a measured reflectance curve.

* * * * *